United States Patent [19]

Durette et al.

[11] 4,377,570
[45] Mar. 22, 1983

[54] IMMUNOLOGICALLY ACTIVE DIPEPTIDYL SACCHARIDES AND METHODS OF PREPARATION

[75] Inventors: Philippe L. Durette, New Providence; Tsung-Ying Shen, Westfield, both of N.J.

[73] Assignee: Merck & Co., Inc., Rahway, N.J.

[21] Appl. No.: 193,777

[22] Filed: Oct. 3, 1980

Related U.S. Application Data

[62] Division of Ser. No. 7,108, Jan. 29, 1979, Pat. No. 4,256,735.

[51] Int. Cl.³ .................. A61K 39/00; A61K 37/02
[52] U.S. Cl. .................................... 424/88; 424/177
[58] Field of Search .................. 260/112.5 R; 424/85, 424/177, 88–92

[56] References Cited

U.S. PATENT DOCUMENTS 4,158,052  6/1979  Audihert et al. .................. 424/88
4,185,089  1/1980  Derrien et al. .................. 424/88

OTHER PUBLICATIONS

Chemical Abstracts, vol. 90, p. 20, Abst. No. 132579p, 1979.

*Primary Examiner*—Blondel Hazel
*Attorney, Agent, or Firm*—Donald J. Perrella; Hesna J. Pfeiffer

[57] ABSTRACT

2-Amino-2-deoxy-glycoses of the general structural formula:

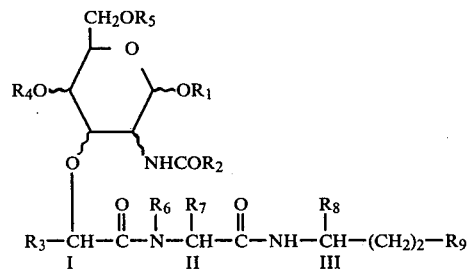

wherein $R_1$ is hydrogen, alkyl (1–7C), substituted alkyl (1–7C), phenyl, substituted phenyl, benzyl, or substituted benzyl;

$R_2$ is alkyl, substituted alkyl, phenyl, or substituted phenyl;

$R_3$ is H or lower alkyl (1–10C) with the proviso that when the aminoglycose has the 2-amino-2-deoxy-D-glucose configuration, $R_3$ cannot be H;

$R_4$ and $R_5$ are same or different and are H, aliphatic or aromatic acyl (2–21C) or substituted acyl (2–21C);

$R_6$ is H, or $R_6$–$R_7$ together is —$CH_2$—$CH_2$—$CH_2$—, $R_7$ is H, alkyl (1–7C), hydroxymethyl, mercaptomethyl, benzyl, or substituted benzyl;

$R_8$ and $R_9$ each is carboxyl, esterified carboxyl (1–7C), amidated carboxyl, or mono- or di-alkyl-(1–3C)-amidated carboxyl;

provided that when $R_3$ is lower alkyl, the stereochemistry at asymmetric center I can be either D or L, but that when the aminoglycose has the 2-amino-2-deoxy-D-glucose configuration, the stereochemistry at I cannot be D;

when $R_7$ is not H, the stereochemistry at asymmetric center II is either L or D; and the stereochemistry at asymmetric center III is D.

These compounds possess immunostimulatory properties.

2 Claims, No Drawings

IMMUNOLOGICALLY ACTIVE DIPEPTIDYL SACCHARIDES AND METHODS OF PREPARATION

This is a division of application Ser. No. 007,108, filed Jan. 29, 1979, now U.S. Pat. No. 4,256,735.

BACKGROUND OF THE INVENTION

One of the most active immunoadjuvants is Freund's Complete Adjuvant which is a water-oil emulsion consisting of 10% Arlacel A and 90% mineral oil containing whole killed mycobacterial cells. A vaccine is formulated with Freund's Complete Adjuvant by incorporating the antigen in the aqueous phase. Therapeutic applications of Fruend's Complete Adjuvant, however, have been prevented due to accompanying toxic side effects such as local granulomas, endotoxic shock, and adjuvant-induced polyarthritis. Subsequently, the minimal active structure of mycobacteria has been determined by Ellouz et al., Biochem. Biophys. Res. Commun., 59, 1317 (1974) and by Kotani et al., *Biken J.*, 18, 105 (1975) to be a peptidoglycan fragment of the cell wall, more specifically, a muramyl dipeptide, namely, N-acetylmuramyl-L-alanyl-D-isoglutamine (MDP). The addition of synthetic MDP to an emulsion of Freund's incomplete adjuvant (90% mineral oil and 10% Arlacel A) containing an antigen increases the level of antibodies against the antigen (humoral response) and induces delayed hypersensitivity (cellular immunity).

The effects of various structural modifications of the dipeptidyl moiety of MDP on biological activity have been reported, although studies on the effects of modifications of the saccharide moiety have been limited.

OBJECTS OF THE INVENTION

It is an object of the present invention to provide biologically active dipeptidyl saccharides having immunostimulatory properties. Another object is to provide methods for the preparation of these compounds. A further object is to provide formulations for incorporating these dipeptidyl saccharides into a vaccine. These and other objects of the present invention will be apparent from the following description.

SUMMARY OF THE INVENTION

2-Amino-2-deoxy-glycoses of the general structural formula:

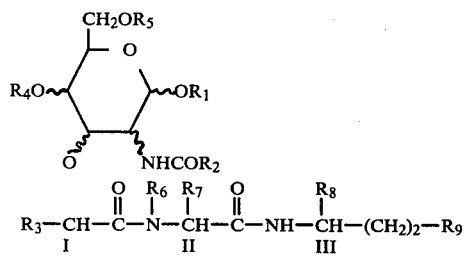

wherein $R_1$ is hydrogen, alkyl (1–7C), substituted alkyl (1–7C), phenyl, substituted phenyl, benzyl, or substituted benzyl;

$R_2$ is alkyl, substituted alkyl, phenyl, or substituted phenyl;

$R_3$ is H or lower alkyl (1–10C) with the proviso that when the aminoglycose has the 2-amino-2-deoxy-D-glucose configuration, $R_3$ cannot be H;

$R_4$ and $R_5$ are same or different and are H, aliphatic or aromatic acyl (2–21C) or substituted acyl (2–21C);

$R_6$ is H, or $R_6$–$R_7$ together is —$CH_2$—$CH_2$—$CH_2$—, $R_7$ is H, alkyl (1–7C), hydroxymethyl, mercaptomethyl, benzyl, or substituted benzyl;

$R_8$ and $R_9$ each is carboxyl, esterified carboxyl (1–7C), amidated carboxyl, or mono- or di-alkyl-(1–3C)-amidated carboxyl;

Provided that when $R_3$ is lower alkyl, the stereochemistry at asymmetric center I can be either D or L, but that when the aminoglycose has the 2-amino-2-deoxy-D-glucose configuration, the stereochemistry at I cannot be D;

When $R_7$ is not H, the stereochemistry at asymmetric center II is either L or D; and The stereochemistry at asymmetric center III is D.

The compounds in the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in Freund's Complete Adjuvant. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific host protection against infectious organisms, for example, *Klebsiella pneumoniae, Candida albicans* or *Staphylococcus aureus*.

DETAILED DESCRIPTION

The prior art chemistry concerning MDP has been concerned, heretofore, mostly with modification of the dipeptidyl moiety, and no analog reported has proved to be more active than MDP itself. The present invention is concerned with immunostimulatory 2-aminoglycoses of the general structural formula:

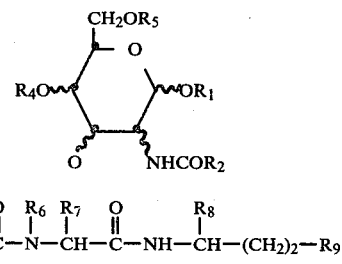

wherein $R_1$ is hydrogen, alkyl (1–7C), substituted alkyl (1–7C), phenyl, substituted phenyl, benzyl, or substituted benzyl;

$R_2$ is alkyl, substituted alkyl, phenyl, or substituted phenyl;

$R_3$ is H or lower alkyl (1–10C) with the proviso that when the aminoglycose has the 2-amino-2-deoxy-D-glucose configuration, $R_3$ cannot be H;

$R_4$ and $R_5$ are same or different and are H, aliphatic or aromatic acyl (2–21C) or substituted acyl (2–21C);

$R_6$ is H, or $R_6$–$R_7$ together is —CH$_2$—CH$_2$—CH$_2$—, $R_7$ is H, alkyl (1–7C), hydroxymethyl, mercaptomethyl, benzyl, or substituted benzyl;

$R^8$ and $R^9$ each is carboxyl, esterified carboxyl (1–7C), amidated carboxyl, or mono- or di-alkyl-(1–3C)-amidated carboxyl;

Provided that when $R_3$ is lower alkyl, the stereochemistry at asymmetric center I can be either D or L, but that when the aminoglycose has the 2-amino-2-deoxy-D-glucose configuration, the stereochemistry at I cannot be D;

When $R_7$ is not H, the stereochemistry at assymetric center II is either L or D; and The stereochemistry at asymmetric center III is D.

The compounds in the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in Freund's Complete Adjuvant. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific host protection against infectious organisms, for example, *Klebsiella pneumoniae*, *Candida albicans* or *Staphylococcus aureus*.

The compounds of formula 1 may be prepared by condensing using conventional procedures a protected compound of formula 2 with a protected compound of formula 3.

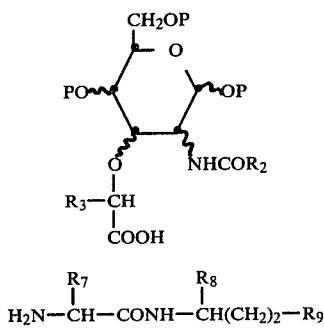

2

3

$$\underset{|}{\overset{R_7}{H_2N-CH}}-CONH-\underset{|}{\overset{R_8}{CH}}(CH_2)_2-R_9$$

In the foregoing formulas, $R_2$, $R_3$, $R_7$, $R_8$ and $R_9$ represent the groups mentioned previously while P is a protecting group. The protecting group may be any suitable to protect the group to which it is attached during the condensation reaction and which may be readily removed thereafter. As protecting groups for the carboxyl group, there may be mentioned tertiary-butyl, benzyl or benzhydryl. For the hydroxyl groups, there may be mentioned the acyl radical, for example, the alkanoyl radical, such as acetyl, the aroyl radical, such as benzoyl, and, in particular, radicals derived from carbonic acid, such as benzyloxycarbonyl or lower alkyloxycarbonyl. Also to be mentioned are alkyl radicals, such as tertiary-butyl, benzyl, nitrobenzyl, lower alkoxy radical, or the tetrahydropyranyl radical. In addition, there may be mentioned the optionally substituted alkylidene radicals that block the oxygen atoms at the C-4 and C-6 positions. Among the alkylidene radicals, one finds, in particular, the lower alkylidene radicals, especially ethylidene, isopropylidene, or propylidene, and also, the optionally substituted benzylidene radical, preferentially substituted at the para position. For a more complete listing of protecting groups, reference may be had to standard works on peptide chemistry, e.g. Bodanszky et al., "Peptide Synthesis", chapter 4, Interscience Publishers, 1966 or Schroeder et al., "The Peptides" Vol. I, pp. xxiii–xxix, Academic Press, 1965, and to the next "Protective Groups in Organic Chemistry", Plenum Press, 1973, J. F. W. McOmie, (ed.).

The condensation is effected by reacting the compound 2 in the form where the carboxylic acid is activated with the amino compound 3. The activated carboxyl group may be, for example, an acid anhydride, preferably, a mixed acid anhydride like an acetate of the acid, an amide of the acid like an imidazolid, an isoxazolid or an activated ester. The activated esters, include the cyanomethyl ester, the carboxylmethyl ester, the p-nitrophenyl thioester, the p-nitrophenyl ester, the 2,4,5-trichlorophenyl ester, the pentachlorophenyl ester, the N-hydroxysuccinimide ester, the N-hydroxyphthalimide ester, the 8-hydroxyquinoline ester, the 2-hydroxy-1,2-dihydro-1-carboethoxyquinoline esters, the N-hydroxypiperidine ester or enol ester derived from N-ethyl-5-phenyl-isoxazolium-3'-sulfonate. The activated esters may equally be obtained from a carbodiimide by addition of N-hydroxysuccinimide or from a substituted 1-hydroxybenzyltriazole for example, a halogen, methyl, or methoxy-substituted 3-hydroxy-4-oxo-3,4-dihydrobenzo-[d]-1,2,3-triazine.

The amino group may be activated, for example, by reaction with a phosphitamide.

Among the methods of reaction with the activated esters, one must mention in particular those that involve N-ethyl-5-phenyl-isoxazolium-3'-sulfonate (Woodward's Reagent K), N-ethoxycarbonyl-2-ethoxy-1,2-dihydroquinoline, or carbodiimide. Upon completion of the coupling reaction, the protecting groups may be removed in conventional manner to yield a compound of formula 1.

The starting materials utilized are known or can be made in a known fashion. Thus, one can obtain compounds of formula 2, for example, by reacting the corresponding sugar unsubstituted at position-3 with a halogen-$R_3$-acetic acid where $R_3$ has the meaning mentioned above. The ether is obtained in the presence of a strong base. The halogen is preferentially bromo or chloro.

Another process of synthesizing these new glycosamine compounds consists of condensation and eventual deblocking in conventional manner of the protecting groups present in a compound of formula 4:

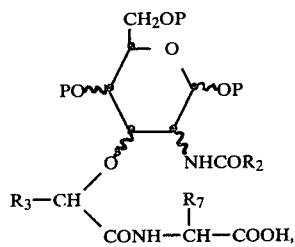

4 wherein $R_2$, $R_3$, and $R_7$ and P have the meaning mentioned above, with a compound of formula 5

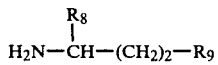
                                                                    5 wherein $R_8$ and $R_9$ have the meaning mentioned above.

The condensation may be effected by reacting compound 4 in the form of an activated carboxylic acid with the amino compound 5 or by reacting 4 in the form of the free C-terminal carboxyl group with compound 5 where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino group may be activated, for example, by reaction with a phosphitamide. The readily removable protecting groups correspond to those mentioned above.

The starting materials are obtained in classical fashion. One can, therefore,, react the corresponding sugar unsubstituted at position-3 with halogen-$R_3$-acetamido-$R_7$-acetic acid or a compound of formula 2 with an amino-$R_7$-acetic acid where the carboxyl group is blocked as mentioned above followed by removal of the protecting groups to give the compound of formula 6.

Another process for inserting the side chain at position-3 of the sugar radical consists in reacting a compound having structure 6

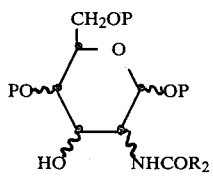
                                                                    6 where $R_2$ and P have the signification mentioned above with a compound of formula 7

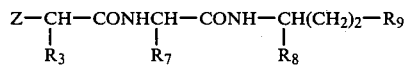
                                                                    7 where Z represents an esterified hydroxy group capable of reacting and wherein $R_3$, $R_7$, $R_8$ and $R_9$ have the meaning given above followed by removal of the protecting groups optionally present. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. One can remove them in a classical fashion, for example, by hydrogenolysis with hydrogen in the presence of a noble metal catalyst, such as palladium or platinum, or by acid hydrolysis. The starting materials utilized in this preparative route are known.

One can also obtain the new compounds by acid hydrolysis of the oxazoline and dioxalane rings in the compound of formula 8,

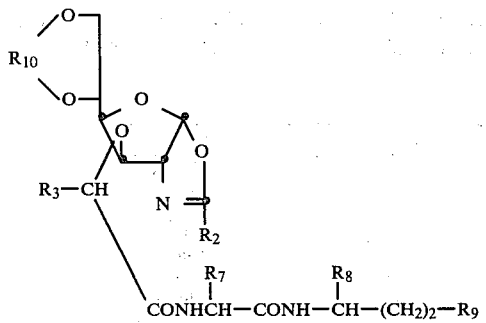
                                                                    8 where $R_2$, $R_3$, $R_7$, $R_8$ and $R_9$ have the meaning mentioned above and where $R_{10}$ is an alkylidene or cycloalkylidene group, and by removing the protecting groups optionally present.

Alkylidene signifies, particularly in this case, a lower alkylidene, such as isopropylidene and cycloalkylidene, especially cyclopentylidene or cyclohexylidene. This hydrolysis is effected equally in a classical fashion, for example, with acidic ion exchange resins, in particular, with an exchange-resin containing sulfonic acid groups like Amberlite IR-120, (resins of styrene containing stongly acidic sulfonyl groups) or Dowex-50 (polystyrene sulfonic acids) or with a strong inorganic or organic acid like hydrochloric acid, hydrobromic acid, sulfuric acid or a sulfonic acid like methanesulfonic acid or a phenylsulfonic acid optionally substituted in its aromatic nucleus, like p-toluenesulfonic acid, or trifluoroacetic acid.

In the presence of water, one obtains at position-1 a free hydroxy group. In the presence of an alcohol of formula $R_1OH$, where $R_1$ represents an optionally substituted alkyl group, one obtains the corresponding $R_1$ substituted compound. If one of the $R_8$ or $R_9$ carboxyl protecting groups P is the moiety resulting from esterifying the carboxyl group with an alcohol, in particular by a lower alcohol, the alcohol may be hydrolyzed, particularly at high temperature, with aqueous acid to liberate the free acid. During this hydrolysis it is possible that the amino group at position-2 of the molecule of the sugar may be liberated. One must in this case lastly insert the group

This is achieved in the usual fashion by acylation. In the resulting compounds, the protecting groups may be removed from the peptide radical, for example, by hydrogenolysis, such as with activated hydrogen in a catalytic fashion, or by hydrolysis. The starting materials utilized here are obtained, for example, by inserting the radical $R_3$-acetamidopeptide in one or several steps in the corresponding oxazoline with a free hydroxy group at position-3 of the sugar radical.

In any of the foregoing methods for the synthesis of the compounds of the present invention, when $R_4$ is greater than acetyl, the desired group is obtained by employing the appropriate acid anhydride or acid halide, preferably the acid chloride, e.g. propionyl chloride, when $R_4$ is propionyl. When $R_4$ is H and $R_5$ is acyl, it is not necessary to protect $R_4$. However, when $R_5$ is hydrogen and $R_4$ is acyl, then $R_5$ must be protected, preferably with trityl ether, before acylating $R_4$ followed by deblocking $R_5$. Compounds wherein $R_7$ is other than methyl, may be obtained when, for example, one of the following amino acids is substituted for alanine:

| Amino acid | $R_7$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_6$ and $R_7$ together are $-CH_2CH_2CH_2-$ are obtained by substituting proline for alanine.

The term "substituted alkyl" for $R_1$ and $R_2$ refers to an alkyl group of from 1 to 7 carbon atoms substituted by hydroxy, mercapto, alkoxy of 1–3 carbons, alkyl mercapto of 1–3 carbons, hydroxy or mercapto esterified by an acid of 1–4 carbon atoms, halogen (F, Cl or Br), carboxyl, or carboxyl functionally modified by esterification with a lower alcohol of 1–3 carbons or by amidation. Preferably the alkyl substituents are hydroxy or mercapto, either free or substituted by an alkyl group of 1–3 carbons.

The substituents in the terms "substituted phenyl" for $R_1$ and $R_2$ or "substituted benzyl" for $R_1$ refer to the phenyl group substituted by one or more alkyl groups of 1–3 carbon carbons or hydroxy or mercapto groups either free, or etherified by an alkyl group of 1–3 carbons or esterified by an acid of 1–4 carbons, lower (1–4C) alkyldioxy, cycloalkyldioxy of 5–7 carbon atoms, amino or trifluoromethyl.

Compounds wherein $R_1$ is hydrogen and $R_2$ is other than methyl are obtained by reacting the appropriate 2-amino-2-deoxy-D-glycose, in the case where $R_2$ is alkyl or substituted-alkyl, with the appropriate alkanoic anhydride or alkanoyl halide, preferably chloride, or substituted-alkanoic anhydride or substituted-alkanoyl halide, preferably chloride, and in the case where $R_2$ is phenyl or substituted-phenyl, with the appropriate aroic anhydride or aroyl halide, preferably chloride, or substituted aroic anhydride or substituted aroyl halide, preferably chloride, in the presence of an appropriate acid acceptor, such as pyridine or triethylamine. The protecting groups P are then introduced at the C-1, C-4, and C-6 positions to give a compound of formula 6 which may then be converted to a compound of formula 2 or formula 4.

In general, compounds wherein $R_1$ is other than hydrogen are prepared by reacting an alcohol of formula $R_1OH$ with the N-alkanoylglycosamine or N-aroylglycosamine to give the corresponding alkyl, substituted alkyl, phenyl, substituted phenyl, benzyl, or substituted benzyl glycopyranoside. The latter are then treated to block the C-4 and C-6 hydroxyl groups, for example, as benzylidene acetal, by reaction with benzyladehyde and boron trifluoride etherate or zinc chloride. The blocked $R_3$-acetamidodipeptide fragment is then inserted into the blocked glycopyranoside having a free hydroxyl group at position-3 of the sugar radical in one or several steps as described above. The protecting groups are then removed by hydrogenolysis with hydrogen in the presence of a noble metal catalyst, or by acid hydrolysis.

The acyl group for $R_4$ and $R_5$ represents an alkanoyl radical and especially an alkanoyl comprising 2 to 21 carbon atoms, like acetyl or propionyl, and also an aroyl like benzoyl, naphthoyl-1 and naphthoyl-2, and, in particular, benzoyl or naphthoyl substituted with halogen, lower alkyl (1–3C), lower alkoxy (1–3C), trifluoromethyl, hydroxy, or lower alkanoyloxy. Acyl also represents a sulfonyl radical of an organic sulfonic acid like alkanesulfonic acid, in particular, a lower alkanesulfonic acid, like methanesulfonic acid or ethanesulfonic acid or an arylsulfonic acid, in particular, a phenylsulfonic acid optionally substituted by a lower alkyl, like benzenesulfonic acid or p-toluenesulfonic acid. Acyl also represents a carbamoyl radical, like a non-substituted carbamoyl, a lower (1–3C) alkylcarbamoyl or arylcarbamoyl, like the methylcarbamoyl or the phenylcarbamoyl.

For $R_8$ and $R_9$, among the optionally esterified carboxyl groups can be mentioned the carboxyl group esterified by a lower alcohol of 1–3 carbons, like methanol or ethanol. The carboxyl group can also be amidated, unsubstituted at the nitrogen atom or mono- or di-substituted with an alkyl, in particular, a lower alkyl, an aryl, particularly phenyl, or an aralkyl, particularly benzyl.

Most preferably, $R_1$ is H, alkyl of 1–3 carbons, benzyl, phenyl or phenyl p-substituted by alkyl (1–3C), amino, halogen, hydroxy or trifluoromethyl; $R_2$ is alkyl of 1–3 carbons, or phenyl, or phenyl p-substituted by alkyl (1–3C), amino, halogen, hydroxy or trifluoromethyl, $R_3$ is H or lower alkyl of 1–3 carbons, $R_4$ and $R_5$ are H, alkanoyl of 2–21 carbons, benzoyl or naphthoyl, $R_7$ is H, alkyl of 1–4 carbons, hydroxymethyl, mercaptomethyl, benzyl or p-hydroxybenzyl, $R_6$ and $R_7$ together are $-CH_2CH_2CH_2-$, and $R_8$ and $R_9$ are carboxyl, carboxyl esterified by an alcohol of 1–4 carbons, carboxamide, or monoalkyl or dialkyl substituted carboxamide wherein the alkyl group has from 1–3 carbons.

The obtained compounds can be transformed to their salts in a classical fashion, for example, by reacting the acidic compounds obtained with alkaline or alkaline earth hydroxides or the basic compounds with acids.

The present invention is also directed to pharmaceutical preparations that contain a compound of formula 1. Among the pharmaceutical preparations relevant to this invention are salts that are administered by external route, for example, orally, rectally or parenterally to mammalian species. Preparations may be administered that contain the pharmacologically active compound by itself or mixed with a pharmaceutically acceptable carrier. The dose of the pharmacologically active compound depends on the animal specie, the age, and the state of the individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA-antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti-BSA antibodies by i.p. or subcutaneous application (s.c.) of 100–300 mg/kg/animal during 5 consecutive days (day 0 to day 4) after immunization with BSA.

The immunostimulatory effect of the compounds mentioned herein depend on the antigen, contrary to other bacterial immunostimulants (like LPS of $E.\ coli$). The injection of the compounds of the present invention results in augmentation of anti-BSA antibody titer only in mice immunized with BSA, and not with non-immunized mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds of the present invention permit specific augmentation of humoral immunity, improve immune response, and provide long-lasting immunostimulatory effects on systemic activation of immune apparatus.

2. Stimulation of Mitotic Responses of Lymphocyte Cultures

Mouse lymphoid cells are cultured in microtiter plates, in RPMI-1640 medium with 2% fetal calf serum. Cultures are set in triplicates and consist of $3-5\times10^5$ spleen or $1.5\times10^6$ thymus cells per well in a final volume of 0.2 ml. Class specific mitogens are added at optimal or suboptimal concentrations, while control cultures are incubated without mitogens. The tested compounds are added shortly after the mitogens and the cultures are incubated for 48 hours at 37° with 5% $CO_2$. Incorporation of tritiated thymidine is determined after a pulse (1.0μ Ci/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose-dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, on the one hand, of being mixed with an antigen for which an increase in immunogenicity is required and on the other hand, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as (1) adjuvants by mixing them with vaccines with the goal of improving the effectiveness of the vaccination and (2) protective agents against infections caused by bacteria, viruses or pathogenic parasites, owing to immunity by humoral antibodies and/or to cellular mediation.

Thus, the described compounds are indicated, mixed with the most varied antigens, as adjuvants for experimental as well as industrial production of antisera for therapeutic and diagnostic purposes, as well as to induce immunologically active lymphocyte populations at the time of cell transfers.

Moreover, one can equally utilize the new compounds without simultaneously supplying antigen in order to enhance immune reactions that are already taking place in a subliminal fashion in a mammalian host. These compounds are therefore especially indicated for stimulation of individual immune defense, e.g., at the time of chronic or acute infections or in cases of selective (antigen-specific) immunological deficiencies as well as in situations of immune deficiency, but also acquired general deficiency (i.e., not antigen-specific) as appears with age, during intial shock from a grave illness, and before and soon after radiation therapy or immunosuppressive hormones. The said compounds can subsequently be administered in combination with antiinfectious antibiotics, chemical therapeutics or other methods of treatment, to combat immunological deficiencies. The described compounds are thus indicated equally for general prophylaxis of infectious disease in man and animal.

The following examples illustrate the present invention without, however, limiting the same thereto. All temperatures are expressed in degrees Celsius.

EXAMPLE 1

Preparation of 2-Acetamido-2-deoxy-3-O-(D-2-propionyl-L-alanyl-D-isoglutamine)-D-galactose Step A Preparation of Benzyl 2-acetamido-4,6-O-benzylidene-2-deoxy-3-O-(D-2-propionyl-L-alanyl-D-isoglutamine benzyl ester)-α-D-galactopyranoside A solution of benzyl 2-acetamido-4,6-O-benzylidene-3-O-(D-1-carboxyethyl)-2-deoxy-α-D-galactopyranoside [prepared by the process set forth in P. Sina and R.

W. Jeanloz, *Carbohyd. Res.* 10, 189 (1969)] (343.2 mg) in freshly distilled tetrahydrofuran (10 ml) is cooled to 0° and treated with stirring with N-hydroxysuccinimide (84.3 mg) and N,N'-dicyclohexylcarbodiimide (152.4 mg). The reaction mixture is stirred at 0° for 3 hours and then at room temperature for 1 hour. The solids formed are filtered off and washed with tetrahydrofuran. The combined filtrates are cooled to 0° and treated with L-alanyl-D-isoglutamine benzyl ester hydrochloride (253.3 mg) and triethylamine (0.11 ml). The reaction mixture is allowed to attain room temperature and then stirred overnight. After evaporation of the solvent, the solid residue is triturated with water, filtered, taken up in N,N-dimethylformamide and adsorbed onto silica gel (2.5 g). The mixture is applied to a column of silica gel (70 g) and eluted with 33:1 chloroform-methanol. The fractions containing the desired product are combined and concentrated to afford benzyl 2-acetamido-4,6-O-benzylidene-2-deoxy-3-O-(D-2-propionyl-L-alanyl-D-isoglutamine benzyl ester)-α-D-galactopyranoside as a white crystalline solid, yield 375.2 mg (68%), m.p. 250°–251°, $[α]_D$ +129° (c 1.0, N,N-dimethylformamide).

STEP B Preparation of 2-Acetamido-2-deoxy-3-O-(D-2-propionyl-L-alanyl-D-isoglutamine)-D-galactose A solution of benzyl 2-acetamido-4,6-O-benzylidene-2-deoxy-3-O-(D-2-propionyl-L-alanyl-D-isoglutamine benzyl ester)-α-D-galactopyranoside (250.3 mg) in glacial acetic acid (10 ml) is hydrogenolyzed in the presence of palladium black at room temperature overnight. The reaction mixture is filtered through Celite, the filtrate evaporated, and traces of acetic acid removed by several coevaporations with toluene. The residue is taken up in the minimal volume of methanol and applied to a column of silica gel and eluted with 80:20:2 $CHCl_3$—MeOH—$H_2O$ and subsequently with 60:40:10 $CHCl_3$—MeOH—$H_2O$. The fractions containing the desired product are combined, concentrated, the residue taken up in water and lyophilized to afford 2-acetamido-2-deoxy-3-O-(D-2-propionyl-L-alanyl-D-isoglutamine)-D-galactose as a white amorphous solid; yield 73 mg (45%); $[α]_D$+44° (c, 0.4, water).

EXAMPLE 2

Preparation of 2-Acetamido-2-deoxy-3-O-(D-2-propionyl-L-alanyl-D-isoglutamine)-D-mannose

Step A Benzyl 2-Acetamido-4,6-O-benzylidene-3-O-(D-1-carboxyethyl)-2-deoxy-α-D-mannopyranoside To a stirred solution of benzyl 2-acetamido-4,6-O-benzylidene-2-deoxy-α-D-mannopyranoside [prepared by the process set forth in J. Yoshimura, H. Sakai, N. Oda, and H. Hashimoto, *Bull. Chem. Soc.* Japan, 45, 2027 (1972)] (0.44 g) in dry dioxane (30 ml) at 95° is added sodium hydride (0.25 g) (50% oil suspension). After 1 hour, the temperature is lowered to 65° and then a solution of L-2-chloropropionic acid (0.26 g) in a small volume of dioxane is added. After 1 hour, an additional 1 g of sodium hydride is added, and heating with stirring at 65° is continued overnight. Water (15 ml) is carefully added to the cooled reaction mixture. A dark-colored lower layer which developed is discarded, and the upper layer is filtered, partially concentrated, and diluted with water (10 ml). The aqueous mixture is extracted with diethyl ether, and the aqueous layer acidified to pH~3 at 0° and extracted with chloroform (3×). The combined organic extracts are dried over anhydrous sodium sulfate and evaporated to give benzyl 2-acetamido-4,6-O-benzylidene-3-O-(D-1-carboxyethyl)-2-deoxy-α-D-mannopyranoside; yield 313 mg. The 300 MHz nmr spectrum in methanol-$d_4$ is in accord with the desired structure.

Step B Preparation of Benzyl 2-acetamido-4,6-O-benzylidene-2-deoxy-3-O-(D-2-propionyl-L-alanyl-D-isoglutamine benzyl ester)-α-D-mannopyranoside To a solution of benzyl 2-acetamido-4,6-O-benzylidene-3-O-(D-1-carboxyethyl)-2-deoxy-α-D-mannopyranoside (251 mg) in dry N,N-dimethylformamide (3 ml) at −15° is added N-methylmorpholine (65 μl) and isobutyl chloroformate (73 μl). After stirring 10 minutes at −15°, a pre-cooled solution of L-alanyl-D-isoglutamine benzyl ester hydrochloride (221 mg) in DMF (2 ml) is added followed by N-methylmorpholine (75 μl). The reaction mixture is stirred at −15° for 4 hours and then allowed to warm to 0°. An aqueous solution of potassium hydrogen carbonate (2.5 M, 3 ml) is added dropwise. The mixture is stirred at 0° for 30 minutes and poured into distilled water (70 ml). The aqueous mixture is neutralized with 2.5 N HCl and concentrated to dryness. The residue is taken up in DMF (10 ml), the insoluble material filtered off, the filtrate adsorbed onto silica gel (2 g) and applied to a column of silica gel and eluted with 29:1 chloroform-methanol. The fractions containing the desired product are combined and concentrated to afford benzyl 2-acetamido-4,6-O-benzylidene-2-deoxy-3-O-(D-2-propionyl-L-alanyl-D-isoglutamine benzyl ester)-α-D-mannopyranoside as a white amorphous solid; yield 92 mg. (23%), $[α]_D$+29° (c 0.55, acetic acid).

Step C Preparation of 2-Acetamido-2-deoxy-3-O-(D-2-propionyl-L-alanyl-D-isoglutamine)-D-mannose A solution of benzyl 2-acetamido-4,6-O-benzylidene-2-deoxy-3-O-(D-2-propionyl-L-alanyl-D-isoglutamine benzyl ester)-α-D-mannopyranoside (86 mg) in glacial acetic acid (6 ml) is hydrogenolyzed in the presence of palladium black at room temperature overnight. The reaction mixture is filtered through Celite, the filtrate evaporated, and traces of acetic acid removed by several coevaporations with toluene. The residue is taken up in a small volume of methanol and the product precipitated by the addition of diethyl ether. The solid is filtered, dissolved in a small volume of water, and lyophilized to afford 2-acetamido-2-deoxy-3-O-(D-2-propionyl-L-alanyl-D-isoglutamine)-D-mannose as a white amorphous solid; yield 40 mg. The 300 MHz nmr spectrum in $D_2O$ is in accord with the desired structure.

EXAMPLE 3

Preparation of 2-acetamido-2-deoxy-3-O-(L-2-propionyl-L-alanyl-D-isoglutamine)-D-glucose

Step A: Preparation of Benzyl 2-acetamido-4,6-O-benzylidene-2-deoxy-3-O-(L-2-propionyl-L-alanyl-D-isoglutamine benzyl ester)-α-D-glucopyranoside To a solution of benzyl 2-acetamido-4,6-O-benzylidene-3-O-(L-1-carboxyethyl)-2-deoxy-α-D- glucopyranoside [prepared by the process set forth in J. M. Petit, P. Sina, E. Walker, D. A. Jeanloz, and R. W. Jeanloz, *Carbohyd Res.*, 24, 415 (1972)] (498.7 mg) in dry N,N-dimethylformamide (3 ml) and hexamethylphosphorictriamide (6 ml) at −15° is added N-methylmorpholine (120 µl) and isobutyl chloroformate (140 µl). After stirring 20 minutes at −15°, a pre-cooled solution of L-alanyl-D-isoglutamine benzyl ester hydrochloride (431.5 mg) in DMF (3 ml) is added.

The reaction mixture is stirred at −15° for 4 hours and then at 0° for 1½ hours. An aqueous solution of potassium hydrogen carbonate (2.5 M, 5 ml) is added dropwise. The mixture is stirred at 0° for 30 minutes and poured into vigorously-stirred distilled water (90 ml). The precipitated white solid is filtered off and washed thoroughly with water and then twice with diethyl ether before being dried in vacuo over phosphorus pentoxide at room temperature overnight to afford benzyl 2-acetamido-4,6-O-benzylidene-2-deoxy-3-O-(L-2-propionyl-L-alanyl-D-isoglutamine benzyl ester)-α-D-glucopyranoside as a white solid; yield 710 mg (88%). The 300 MHz nmr spectrum in DMSO-$d_6$ is in accord with the desired structure.

Step B: Preparation of 2-acetamido-2-deoxy-3-O-(L-2-propionyl-L-alanyl-D-isoglutamine)-D-glucose A solution of benzyl 2-acetamido-4,6-O-benzylidene-2-deoxy-3-O-(L-2-propionyl-L-alanyl-D-isoglutamine benzyl ester)-α-D-glucopyranoside (230 mg) in glacial acetic acid (10 ml) is hydrogenolyzed in the presence of palladium added in the form of PdO (0.20 g) at room temperature overnight. The reaction mixture is filtered through Celite, the filtrate evaporated, and traces of acetic acid removed by several coevaporations with toluene. The residue is taken up in a small volume of methanol and applied to a column of silica gel (20 g) and eluted with 70:40:5 chloroform-methanol-water. The fractions containing the desired product are combined and concentrated. The residue is taken up in a small volume of water, insoluble material is filtered off, and the filtrate is lyophilized to afford 2-acetamido-2-deoxy-3-O-(L-2-propionyl-L-alanyl-D-isoglutamine)-D-glucose as a white amorphous solid; yield 75 mg (50%); $[\alpha]_D -20°$ (C 0.40, water).

EXAMPLE 4

Preparation of 2-benzamido-2-deoxy-3-O-(L-2-propionyl-L-alanyl-D-isoglutamine)-D-glucose

Step A: Preparation of benzyl 2-benzamido-4,6-O-benzylidene-3-O-(L-1-carboxyethyl)-2-deoxy-α-D-glucopyranoside To a stirred solution of benzyl 2-benzamido-4,6-O-benzylidene-2-deoxy-α-D-glucopyranoside [prepared by the process set forth in P. H. Gross and R. W. Jeanloz, *J. Org. Chem.*, 32, 2759 (1967)] (1.16 g) in freshly distilled dioxane (70 ml) at 95° is added sodium hydride (0.57 g, 50% oil suspension). After one hour, the temperature is lowered to 65° and then a solution of D-2-chloropropionic acid (0.42 g) in a small volume of dry dioxane is added. After one hour, additional 50% sodium hydride (2.2 g) is added, and stirring at 65° is continued overnight. Water (35 ml) is carefully added to the cooled mixture to decompose excess sodium hydride. A dark-colored lower layer which develops is discarded, and the upper layer is filtered, partially concentrated, and diluted with water (20 ml). The aqueous mixture is extracted with chloroform and then the aqueous layer is acidified to pH 3 at 0° by addition of 2.5 N HCl and extracted with chloroform (3×). The combined chloroform extracts (of the acidified aqueous mixture) are dried (sodium sulfate) and evaporated to afford syrupy benzyl 2-benzamido-4,6-O-benzylidene-3-O-(L-1-carboxyethyl)-2-deoxy-α-D-glucopyranoside (835 mg). The 300 MHz nmr spectrum in chloroform-d is in accord with the desired structure.

Step B: Preparation of benzyl 2-benzamido-4,6-O-benzylidene-2-deoxy-3-O-(L-2-propionyl-L-alanyl-D-isoglutamine benzyl ester)-α-D-glucopyranoside To a solution of benzyl 2-benzamido-4,6-O-benzylidene-3-O-(L-1-carboxyethyl)-2-deoxy-α-D-glucopyranoside (564 mg) in dry N,N-dimethylformamide (5 ml) at −15° are added successively N-methylmorpholine (120 µl) and isobutyl chloroformate (140 µl). After stirring 3 minutes at −15°, a precooled solution of L-alanyl-D-isoglutamine benzyl ester hydrochloride (432 mg) in DMF (5 ml) is added. The reaction mixture is stirred at −15° for 4 hours and the temperature increased to 0°. An aqueous solution of potassium hydrogen carbonate (2.5 M, 5 ml) is added dropwise and the mixture is stirred at 0° for 30 minutes and then poured into vigorously stirred distilled water (90 ml). The precipitated white solid is filtered, washed thoroughly with water and then with diethyl ether before being dried in vacuo over phosphorous pentoxide at room temperature overnight to afford benzyl 2-benzamido-4,6-O-benzylidene-2-deoxy-3-O-(L-2-propionyl-L-alanyl-D-isoglutamine benzyl ester)-α-D-glucopyranoside as a white solid; yield 803 mg (88%). The 300 MHz nmr spectrum in DMSO-$d_6$ is in accord with the desired structure.

Step C: Preparation of 2-benzamido-2-deoxy-3-O-(L-2-propionyl-L-alanyl-D-isoglutamine)-D-glucose A solution of benzyl 2-benzamido-4,6-O-benzylidene-2-deoxy-3-O-(L-2-propionyl-L-alanyl-D-isoglutamine benzyl ester)-α-D-glucopyranoside (250 mg) in glacial acetic acid (15 ml) is hydrogenolyzed in the presence of palladium black added in the form of palladium oxide (200 mg) at room temperature for 24 hours. The reaction mixture is then filtered through Celite, the filtrate evaporated, and traces of acetic acid removed by several coevaporations with toluene. The residue is taken up in a small volume of methanol and the product precipitated by addition of diethyl ether. 2-Benzamido-2-deoxy-3-O-(L-2-propionyl-L-alanyl-D-isoglutamine)-D-glucose is obtained as a amorphous solid; yield 140 mg. The 300 MHz nmr spectrum in $D_2O$ is in accord with the desired structure.

EXAMPLE 5

Preparation of 2-acetamido-2-deoxy-3-O-(D-2-propionyl-D-alanyl-D-isoglutamine)-D-galactose

Step A: Preparation of Benzyl 2-acetamido-4,6-O-benzylidene-2-deoxy-3-O-(D-2-propionyl-D-alanyl-D-isoglutamine benzyl ester)-α-D-galactopyranoside A solution of benzyl 2-acetamido-4,6-O-benzylidene-3-O-(D-1-carboxyethyl)-2-deoxy-α-D-galactopyranoside [prepared by the process set forth in P. Sina and R. W. Jeanloz, *Carbohyd. Res.*, 10, 189 (1969)] (432 mg) in dry N,N-dimethylformamide (4 ml) and hexamethylphosphorictriamide (1 ml) is cooled to −15° and treated with N-methylmorpholine (110 μl) and isobutyl chloroformate (125 μl). After stirring 15 minutes at −15°, a pre-cooled solution of D-alanyl-D-isoglutamine benzyl ester hydrochloride (341 mg) in 4 ml DMF is added follwd by N-methylmorpholine (120 μl). The reaction mixture is allowed to stir at −15° for 3 hours and then allowed to warm to 0°. An aqueous solution of potassium hydrogen carbonate (2.5 M, 3 ml) is added dropwise. The mixture is stirred at 0° for 30 minutes, and poured into distilled water (100 ml). The aqueous mixture is stirred at room temperature overnight, and the resulting solid material is filtered off, washed thoroughly with water and then with diethyl ether. Drying in vacuo over phosphorus pentoxide overnight affords benzyl 2-acetamido-4,6-O-benzylidene-2-deoxy-3-O-(D-2-propionyl-D-alanyl-D-isoglutamine benzyl ester)-α-D-galactopyranoside as a white solid; yield 615 mg (88%), m.p. 199°–209°, $[\alpha]_D = +107°$ (c 1.03 DMF).

Step B: Preparation of 2-acetamido-2-deoxy-3-O-(D-2-propionyl-D-alanyl-D-isoglutamine)-D-galactose A solution of benzyl 2-acetamido-4,6-O-benzylidene-2-deoxy-3-O-(D-2-propionyl-D-alanyl-D-isoglutamine benzyl ester)-α-D-galactopyranoside (400 mg) in glacial acetic acid (10 ml) is hydrogenolyzed at atmospheric pressure and room temperature in the presence of palladium (added as PdO) over the course of seven days (several additions and one change with fresh palladium oxide are made; total present at any one time is 0.10–0.25 g). The reaction mixture is filtered through Celite, the filtrate evaporated, and traces of acetic acid removed by several coevaporations with toluene. The residue is taken up into a small volume of methanol and applied to a column of silica gel (35 g) and eluted with 70:40:5 chloroform-methanol-water. The fractions containing the desired product are combined and concentrated. The residue is taken up in a small volume of methanol and precipitated by addition of diethyl ether. The solid is filtered, dissolved in water (2 ml) and lyophilized to afford 2-acetamido-2-deoxy-3-O-(D-2-propionyl-D-alanyl-D-isoglutamine)-D-galactose as a white amorphous solid; yield 75 mg (29%). The 300 MHz nmr spectrum in $D_2O$ is in accord with the desired structure.

EXAMPLE 6

Preparation of 2-acetamido-2-deoxy-3-O-(D-2-propionyl-L-seryl-D-isoglutamine)-D-galactose Step A: Preparation of benzyl 2-acetamido-4,6-O-benzylidene-2-deoxy-3-O-(D-2-propionyl-L-(O-benzyl)seryl-D-isoglutamine benzyl ester)-α-D-galactopyranoside A solution of benzyl 2-acetamido-4,6-O-benzylidene-3-O-(D-1-carboxyethyl)-2-deoxy-α-D-galactopyranoside [prepared by the process set forth in P. Sina and R. W. Jeanloz, *Carbohyd. Res.* 10, 189 (1969)] (500 mg) in dry N,N-dimethylformamide (4 ml) is cooled to −15° and 120 μl of N-methylmorpholine and 140 μl of isobutyl chloroformate is added. After stirring 20 minutes at −15°, a pre-cooled solution of O-benzyl-L-seryl-D-isoglutamine benzyl ester hydrochloride (557 mg) in DMF (4 ml) with N-methylmorpholine (140 μl) is added. The reaction mixture is stirred at −15° for 2½ hours and then allowed to warm to 0°. An aqueous solution of potassium hydrogen carbonate (2.5 M, 3 ml) is added dropwise. The mixture is stirred at 0° for 30 minutes and then poured into distilled water (80 ml). The precipitated material is filtered off and washed with several portions of water. The white material is ground to a powder and dried in vacuo over phosphorus pentoxide to afford benzyl 2-acetamido-4,6-O-benzylidene-2-deoxy-3-O-(D-2-propionyl-L-(O-benzyl)-seryl-D-isoglutamine benzyl ester)-α-D-galactopyranoside as a white solid; yield 800 mg (87%), m.p. 129°–131° (from DMF/95% EtOH), $[\alpha]_D + 111°$ (c 1.0, DMF).

Step B: Preparation of 2-acetamido-2-deoxy-3-O-(D-2-propionyl-L-seryl-D-isoglutamine)-D-galactose A solution of benzyl 2-acetamido-4,6-O-benzylidene-2-deoxy-3-O-(D-2-propionyl-L-(O-benzyl) seryl-D-isoglutamine benzyl ester)-α-D-galactopyranoside (596.7 mg) in glacial acetic acid (10 ml) is hydrogenolyzed at room temperature in the presence of palladium [added as PdO, 0.30 g]. The reaction is incomplete after 20 hours; therefore, the catalyst is filtered off through Celite and to the filtrate is added 10% palladium-on-charcoal (0.5 g) and the hydrogenolysis is continued under 40 p.s.i. hydrogen. After 20 hours, the reaction is interrupted, the catalyst is filtered off through Celite, the filtrate is charged with fresh 10% palladium-on-charcoal (0.5 g) and the reaction is continued for another 20 hours under 40 p.s.i. hydrogen. The catalyst is filtered off through Celite, the filtrate evaporated, and traces of acetic acid removed by several coevaporations with toluene. The residue is taken up in a small volume of methanol and adsorbed onto silica gel (40 g) and eluted successively with 9:1 $CHCl_3/MeOH$ and 70:40:8 $CHCl_3/MEOH/H_2O$. The fractions containing the desired product are combined and concentrated. The residue is taken up in a small volume of water, filtered through sintered glass, and lyophilized to afford 2-acetamido-2-deoxy-3-O-(D-2-propionyl-L-seryl-D-isoglutamine)-D-galactose as a white amorphous solid; yield 106 mg (30%). The 300 MHz nmr spectrum in $D_2O$ is in accord with the desired structure.

EXAMPLE 7

2-Acetamido-2-deoxy-3-O-(D-2-propionyl-L-phenylalanyl-D-isoglutamine)-D-galactose In like manner, substituting a stoichiometric equivalent amount of L-phenylalanyl-D-isoglutamine benzyl ester hydrochloride in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-L-phenylalanyl-D-isoglutamine benzyl ester)-α-D-galactopyranoside and subsequently the deprotected dipeptidyl saccharide, 2-acetamido-2-deoxy-3-O-(D-2-propionyl-L-phenylalanyl-D-isoglutamine)-D-galactose.

EXAMPLE 8

2-Acetamido-2-deoxy-3-O-(D-2-propionyl-L-prolyl-D-isoglutamine)-D-galactose

In like manner, substituting a stoichiometric equivalent amount of L-prolyl-D-isoglutamine benzyl ester hydrochloric in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-L-prolyl-D-isoglutamine benzyl ester)-α-D-glactopyranoside and subsequently the deprotected dipeptidyl saccharide, 2-acetamido-2-deoxy-3-O-(D-2-propionyl-L-prolyl-D-isoglutamino)-D-galactose.

EXAMPLE 9

2-Acetamido-2-deoxy-3-O-(D-2-propionyl-L-tyrosyl-D-isoglutamine)-D-galactose

In like manner, substituting a stoichiometric equivalent amount of O-benzyl-L-tyrosyl-D-isoglutamine benzyl ester hydrochloride in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-O-benzyl-L-tyrosyl-D-isoglutamine benzyl ester)-α-D-galactopyranoside and subsequently the deprotected dipeptidyl saccharide, 2-acetamido-2-deoxy-3-O-(D-2-propionyl-L-tyrosyl-D-isoglutamine)-D-galactose.

EXAMPLE 10

2-Acetamido-2-deoxy-3-O-(D-2-propionyl-L-cysteinyl-D-isoglutamine)-D-galactose

In like manner, substituting a stoichiometric equivalent amount of S-benzyl-L-cysteinyl-D-isoglutamine benzyl ester hydrochloride in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-S-benzyl-L-cysteinyl-D-isoglutamine benzyl ester)-α-D-galactopyranoside and subsequently the deprotected dipeptidyl saccharide, 2-acetamido-2-deoxy-3-O-(D-2-propionyl-L-cysteinyl-D-isoglutamine)-D-galactose.

EXAMPLE 11

Preparation of 2-acetamido-2-deoxy-3-O-(L-2-propionyl-L-alanyl-D-isoglutamine)-D-galactose Part A: Preparation of benzyl 2-acetamido-4,6-O-benzylidene-2-deoxy-3-O-(L-2-propionyl-L-alanyl-D-isoglutamine benzyl ester)-α-D-glactopyranoside To a solution of benzyl 2-acetamido-4,6-O-benzylidene-3-O-(L-1-carboxyethyl)-2-deoxy-α-D-galactopyranoside [prepared by the process set forth in P. Sina and R. W. Jeanloz, *Carbohyd. Res.*, 10, 189 (1969)] (605 mg) in dry N,N-dimethylformamide (6 ml) at −15° is added N-methylmorpholine (145 μl) and isobutyl chloroformate (170 μl). After stirring 20 minutes at −15°, a pre-cooled solution of L-alanyl-D-isoglutamine benzyl ester hydrochloride (515 mg) with N-methylmorpholine (170 μl) in DMF (6 ml) is added. The reaction mixture is stirred at −15° for 4 hours, after which it is allowed to warm to 0°. An aqueous solution of potassium hydrogen carbonate (2.5 M, 6 ml) is added dropwise. The mixture is stirred at 0° for 30 minutes and then poured into vigorously stirred water (100 ml). A gummy solid is deposited on the sides of the flask. The creamy supernatant is decanted off and the remaining gum crystallized by trituration with diethyl ether. The supernatant emulsion is extracted once with diethyl ether and three times with ethyl acetate. The combined ethyl acetate extracts are washed once with water and concentrated. The residue is taken up in DMF and combined with a DMF solution of the previously crystallized material. The solution is concentrated to a syrup which is taken up in a small volume of 25:1 chloroform-methanol and applied to a column of silica gel (75 g). Elution with 25:1 chloroform-methanol followed by combination and concentration of the appropriate fractions affords benzyl 2-acetamido-4,6-O-benzylidene-2-deoxy-3-O-(L-2-propionyl-L-alanyl-D-isoglutamine benzyl ester)-α-D-galactopyranoside as a white solid; yield 542 mg (56%). The 300 MHz nmr spectrum in DMSO-$d_6$ is in accord with the desired structure.

Part B: Preparation of 2-acetamido-2-deoxy-3-O-(L-2-propionyl-L-alanyl-D-isoglutamine)-D-galactose A solution of benzyl 2-acetamido-4,6-O-benzylidene-2-deoxy-3-O-(L-2-propionyl-L-alanyl-D-isoglutamine benzyl ester)-α-D-galactopyranoside (355 mg) in glacial acetic acid (10 ml) is hydrogenolyzed in the presence of palladium (added in the form of PdO, 0.20 g) at room temperature for 3 days. The reaction mixture is filtered through Celite, the filtrate is diluted to 15 ml with glacial acetic acid, 10% palladium-on-charcoal (0.4 g) is added, and hydrogenolysis is continued with shaking under 40 p.s.i. hydrogen overnight. The mixture is filtered through Celite and the filtrate is evaporated, with several co-evaporations with toluene, to remove traces of acetic acid. Minor impurities are removed by chromatography over silica gel and elution with 60:40:10 chloroform-methanol-water. The residue is taken up in a minimal volume of methanol and precipitated by addition of ethyl ether. The solid is filtered, dissolved in a small volume of water, and lyophilized to afford 2-acetamido-2-deoxy-3-O-(L-2-propionyl-L-alanyl-D-isoglutamine)-D-galactose as an amorphous white solid, yield 165 mg (72%). The 300 MHz nmr spectrum in $D_2O$ is in accord with the desired structure.

EXAMPLE 12

Preparation of 2-acetamido-2-deoxy-3-O-(D-2-propionyl-L-alanyl-D-isoglutamine)-D-allose Step A: Preparation of benzyl 2-acetamido-4,6-O-benzylidene-3-O-(D-1-carboxyethyl)-2-deoxy-α-D-allopyranoside To a stirred solution of benzyl 2-acetamido-4,6-O-benzylidene-2-deoxy-α-D-allopyranoside [prepared by the process set forth in W. Meyer zu Reckendorf, *Chem. Ber.* 102, 4207 (1969)] (1.00 g) in dry dioxane (70 ml) at 95° is added sodium hydride (0.57 g, 50% oil suspension). After one hour, the temperature is lowered to 65° and then a solution of L-2-chloropropionic acid (0.41 g) in a small volume of dioxane is added. After one hour, additional 50% sodium hydride (2.3 g) is added, and stirring at 65° is continued overnight. Water (35 ml) is carefully added to the cooled reaction mixture. A dark-colored lower layer which develops is discarded, and the upper layer is filtered, partially concentrated, and diluted with water (20 ml). The aqueous mixture is extracted with chloroform and then the aqueous layer is acidified to pH ~3 at 0° by addition of 2.5 N HCl and extracted with chloroform (3x). The combined chloroform extracts (of the acidified aqueous mixture) are dried over anhydrous sodium sulfate and concentrated to give a yellow gummy residue (720 mg) consisting of benzyl 2-acetamido-4,6-O-benzylidene-3-O-(D-1-carboxyethyl)-2-deoxy-α-D-allopyranoside of sufficient purity for subsequent reaction (Step B). An analytical sample is obtained by applying the product mixture (279 mg) to preparative thin-layer chromatography silica gel plates (3 Analtech 1000 μm silica gel GF, 8×8") and developing with 9:1 chloroform-methanol. Extraction of the silica gel band containing the desired product with 9:1 chloroform-methanol, decolorization of the combined extracts with activated charcoal, and concentration affords a glass (131 mg). The 300 MHz nmr spectrum in methanol-d$_4$ is consistent with the desired structure.

Step B: Preparation of benzyl 2-acetamido-4,6-O-benzylidene-2-deoxy-3-O-(D-2-propionyl-L-alanyl-D-isoglutamine benzyl ester)-α-D-allopyranoside To a solution of benzyl 2-acetamido-4,6-O-benzylidene-3-O-(D-1-carboxyethyl)-2-deoxy-α-D-allopyranoside (459 mg) in dry N,N-dimethylformamide (4 ml) at −15° is added N-methylmorpholine (110 μl) and isobutyl chloroformate (130 μl). After stirring 15 minutes at −15°, a pre-cooled solution of L-alanyl-D-isoglutamine benzyl ester hydrochloride (389 mg) in DMF (4 ml) is added, followed by N-methylmorpholine (130 μl). The reaction mixture is stirred at −15° for 3½ hours and then allowed to warm to 0°. An aqueous solution of potassium hydrogen carbonate (2.5 M, 3 ml) is added dropwise. The mixture is stirred at 0° for 30 minutes and poured into distilled water (100 ml). The aqueous mixture is neutralized with 2.5 N HCl and concentrated to dryness. The residue is taken up in DMF (10 ml), the insoluble material filtered off, and the filtrate concentrated to a syrup.

Purification is achieved by applying the material on a column of silica gel packed with 5:1 chloroform-diethyl ether and elution with 20:10:1 chloroform-diethyl ether-methanol. The fractions containing the desired product are combined and concentrated to afford solid benzyl 2-acetamido-4,6-O-benzylidene-2-deoxy-3-O-(D-2-propionyl-L-alanyl-D-isoglutamine benzyl ester)-α-D-allopyranoside; yield 246 mg (33%). The 300 MHz nmr spectrum in DMSO-d$_6$ is in accord with the desired structure.

Step C: Preparation of 2-acetamido-2-deoxy-3-O-(D-2-propionyl-L-alanyl-D-isoglutamine)-D-allose A solution of benzyl 2-acetamido-4,6-O-benzylidene-3-O-(D-2-propionyl-L-alanyl-D-isoglutamine benzyl ester)-α-D-allopyranoside (200 mg) in glacial acetic acid (10 ml) is hydrogenolyzed in the presence of palladium black at room temperature overnight. The reaction mixture is filtered through Celite, the filtrate evaporated, and traces of acetic acid removed by several coevaporations with water and subsequently toluene. The residue is taken up in methanol, filtered, and concentrated to a material that is dissolved in a small volume of water and lyophilized to afford 2-acetamido-2-deoxy-3-O-(D-2-propionyl-L-alanyl-D-isoglutamine)-D-allose as a white amorphous solid; yield 115 mg. The 300 MHz nmr spectrum in D$_2$O is in accord with the desired structure.

EXAMPLE 13

Preparation of 2-acetamido-2-deoxy-3-O-(L-2-propionyl-L-seryl-D-isoglutamine)-D-galactose Step A: Preparation of benzyl 2-acetamido-4,6-O-benzylidene-2-deoxy-3-O-(L-2-propionyl-L-(O-benzyl)seryl-D-isoglutamine benzyl ester)α-D-galactopyranoside To a solution of benzyl 2-acetamido-4,6-O-benzylidene-3-O-(L-1-carboxyethyl)-2-deoxy-α-D-galactopyranoside [prepared by the process set forth in P. Sinay and R. W. Jeanloz, Carbohyd. Res., 10, 189 (1969)] (700 mg) in dry N,N-dimethylformamide (7 ml) at −15° is added N-methylmorpholine (170 μl) and isobutyl chloroformate (200 μl). After stirring 20 minutes at −15°, a pre-cooled solution of O-benzyl-L-seryl-D-isoglutamine benzyl ester hydrochloride (781 mg) in DMF (7 ml) and N-methylmorpholine (200 μl) is added. The reaction mixture is stirred at −15° for 4 hours, and allowed to warm to 0°. An aqueous solution of potassium hydrogen carbonate (2.5 M, 7 ml) is added dropwise. The mixture is stirred at 0° for 30 minutes and poured into vigorously stirred distilled water (120 ml). The precipitated material is filtered off, washed thoroughly with water and diethyl ether before drying in vacuo over phosphorus pentoxide at room temperature overnight to afford benzyl 2-acetamido-4,6-O-benzylidene-2-deoxy-3-O-[L-2-propionyl-L-(O-benzyl)-seryl-D-isoglutamine benzyl ester]-α-D-galactopyranoside as a white solid; yield 1.15 g (85%), m.p. 187°–196°; the 300 MHz nmr in DMSO-d$_6$ is in accord with the desired structure.

Step B: Preparation of 2-acetamido-2-deoxy-3-O-(L-2-propionyl-L-seryl-D-isoglutamine)-D-galactose A solution of benzyl 2-acetamido-4,6-O-benzylidene-2-deoxy-3-O-[L-2-propionyl-L-(O-benzyl)-seryl-D-isoglutamine benzyl ester]-α-D-galactopyranoside (599 mg) in glacial acetic acid (10 ml) is hydrogenolyzed in the presence of palladium (added in the form of PdO, 0.30 g) at room temperature for five days. The reaction mixture is filtered through Celite, the filtrate diluted to 15 ml with glacial acetic acid, and the hydrogenolysis is continued by shaking with 10% palladium-on-charcoal (0.5 g) under 40 p.s.i. hydrogen overnight. The reaction mixture is filtered through Celite, the filtrate concentrated and traces of acetic acid are removed by several co-evaporations with toluene. The residue is taken up in a small volume of methanol and applied to a column of silica gel (35 g). Elution with 9:1 chloroform-methanol, 80:20:2 chloroform-methanol-water, and 60:40:10 chloroform-methanol-water, successively, followed by combination and concentration of the fractions containing the desired product affords a residue which is taken up in a small volume of methanol. Precipitation with addition of diethyl ether, filtration, dissolution of the solid in water, and lyophilization affords 2-acetamido-2-deoxy-3-O-(L-2-propionyl-L-seryl-D-isoglutamine)-D-galactose as a white amorphous solid; yield 115 mg (33%). The 300 MHz nmr spectrum in D$_2$O is in accord with the desired structure.

EXAMPLE 14

Preparation of
2-acetamido-2-deoxy-3-O-(L-2-propionyl-L-seryl-D-isoglutamine)-D-glucose

Step A: Preparation of benzyl 2-acetamido-4,6-O-benzylidene-2-deoxy-3-O-(L-2-propionyl-L-alanyl-D-isoglutamine benzyl ester)-α-glucopyranoside To a solution of benzyl 2-acetamido-4,6-O-benzylidene-3-O-(L-1-carboxyethyl)-2-deoxy-α-D-glucopyranoside [prepared by the process set forth in J. M. Petit, P. Sina, E. Walker, D. A. Jeanloz, and R. W. Jeanloz, *Carbohyd. Res.*, 24, 415 (1972)] (699.5 mg) in dry N,N-dimethylformamide (10 ml) and hexamethylphosphorictriamide (5 ml) at −15° is added N-methylmorpholine (170 μl) and isobutyl chloroformate (200 μl). After stirring 20 minutes at −15°, a pre-cooled solution of L-alanyl-D-isoglutamine benzyl ester hydrochloride (776.8 mg) and N-methylmorpholine (195 μl) in 7 ml DMF is added. The reaction mixture is stirred at −15° for 4 hours and stored at −17° overnight. The temperature is then allowed to rise to 0° and an aqueous solution of potassium hydrogen carbonate (2.5 M, 7 ml) is added dropwise with stirring. The mixture is stirred at 0° for 30 minutes and then poured into 150 ml stirred distilled water. The precipitated material is filtered off and washed thoroughly with water and then with diethyl ether before drying in vacuo over phosphorus pentoxide overnight to afford benzyl 2-acetamido-4,6-O-benzylidene-2-deoxy-3-O-(L-2-propionyl-L-alanyl-D-isoglutamine benzyl ester)-α-D-glucopyranoside as a white solid. The 300 MHz spectrum in DMSO-$d_6$ is in accord with the desired structure.

Step B: Preparation of 2-acetamido-2-deoxy-3-O-(L-2-propionyl-L-seryl-D-isoglutamine)-D-glucose A solution of benzyl 2-acetamido-4,6-O-benzylidene-2-deoxy-3-O-(L-2-propionyl-L-alanyl-D-iso-glutamine benzyl ester)-α-D-glucopyranoside (623 mg) in glacial acetic acid (10 ml) is hydrogenolyzed at room temperature in the presence of palladium (added in the form of palladium oxide, 0.30 g) for 3 days. The reaction mixture is then filtered through Celite, the filtrate diluted to 25 ml with glacial acetic acid, 10% palladium-on-charcoal (0.5 g) is added, and the mixture is shaken under 40 p.s.i. hydrogen overnight. The reaction mixture is again filtered through Celite, evaporated, and coevaporated with toluene several times in order to remove traces of acetic acid. The residue is taken up in a small volume of methanol, applied to a column of silica gel (50 g), and eluted with 80:20:2 chloroform-methanol-water followed by 60:40:10 chloroform-methanol-water. Fractions containing the desired product are combined and concentrated. The residue is taken up in a small volume of methanol, precipitated by addition of diethyl ether, filtered, taken up in a small volume of water, and lyophilized to afford 2-acetamido-2-deoxy-3-O-(L-2-propionyl-L-seryl-D-isoglutamine)-D-glucose as a white amorphous solid; yield 119 mg (32.6%). The 300 MHz nmr spectrum in $D_2O$ is in accord with the desired structure.

EXAMPLE 15

2-Acetamido-2-deoxy-3-O-(L-2-propionyl-L-α-aminobutyryl-D-isoglutamine)-D-glucose In like manner, substituting a stoichiometric equivalent amount of L-α-aminobutyryl-D-isoglutamine benzyl ester hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-L-α-aminobutyryl-D-isoglutamine benzyl ester)-α-D-glucopyranoside and subsequently the deprotected dipeptidyl saccharide, 2-acetamido-2-deoxy-3-O-(L-2-propionyl-L-α-aminobutyryl-D-isoglutamine)-D-glucose.

EXAMPLE 16

2-Acetamido-2-deoxy-3-O-(L-2-propionyl-L-norvalyl-D-isoglutamine)-D-glucose

In like manner, substituting a stoichiometric equivalent amount of L-norvalyl-D-isoglutamine benzyl ester hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-L-norvalyl-D-isoglutamine benzyl ester)-α-D-glucopyranoside and subsequently the deprotected dipeptidyl saccharide, 2-acetamido-2-deoxy-3-O-(L-2-propionyl-L-norvalyl-D-isoglutamine)-D-glucose.

EXAMPLE 17

2-Acetamido-2-deoxy-3-O-(L-2-propionyl-L-norleucyl-D-isoglutamine)-D-glucose

In like manner, substituting a stoichiometric equivalent amount of L-norleucyl-D-isoglutamine benzyl ester hydrochloride in Example 14 for L-alanyl-D-isoglutamine benzyl ester hydrochloride there are obtained the protected glycopeptide derivative, benzyl 2-acetamido-2-deoxy-3-O-(L-2-propionyl-L-norleucyl-D-isoglutamine benzyl ester)-α-D-glucopyranoside and subsequently the deprotected dipeptidyl saccharide, 2-acetamido-2-deoxy-3-O-(L-2-propionyl-L-norleucyl-D-isoglutamine)-D-glucose.

EXAMPLE 18

2-Acetamido-2-deoxy-3-O-(L-2-propionyl-L-alanyl-D-glutamic acid)-D-glucose

In like manner, substituting a stoichiometric equivalent amount of L-alanyl-D-glutamic acid dibenzyl ester hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-L-alanyl-D-glutamic acid di-benzyl ester)-α-D-glucopyranoside and subsequently the deprotected dipeptidyl saccharide, 2-acetamido-2-deoxy-3-O-(L-2-propionyl-L-alanyl-D-glutamic acid)-D-glucose.

EXAMPLE 19

2-Acetamido-2-deoxy-3-O-(L-2-propionyl-L-alanyl-D-glutamic acid dimethyl ester)-D-glucose In like manner, substituting a stoichiometric equivalent amount of L-alanyl-D-glutamic acid dimethyl ester hydrochloride in Example 14 for L-alanyl-D-isoglutamine benzyl ester hydrochloride, there are obtained the protected glycopeptide derivative, benzyl 2-acetamido- 2-deoxy-3-O-(L-2-propionyl-L-alanyl-D-glutamic acid dimethyl ester)-α-D-glucopyranoside and subsequently the deprotected dipeptidyl saccharide, 2-acetamido-2-deoxy-3-O-(L-2-propionyl-L-alanyl-D-glutamic acid dimethyl ester)-D-glucose.

EXAMPLE 20

2-Acetamido-2-deoxy-3-O-(L-2-propionyl-L-alanyl-D-glutamic acid methylamide)-D-glucose In like manner, substituting a stoichiometric equivalent amount of L-alanyl-D-glutamic acid methylamide hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-L-alanyl-D-glutamic acid methylamide)-α-D-glucopyranoside, and subsequently the deprotected dipeptidyl saccharide, 2-acetamido-2-deoxy-3-O-(L-2-propionyl-L-alanyl-D-glutamic acid methylamide)-D-glucose.

EXAMPLE 21

Preparation of 2-acetamido-2-deoxy-3-O-(D-2-propionyl-L-alanyl-D-isoglutamine)-6-O-stearoyl-D-allose

Step A: Preparation of benzyl 2-acetamido-2-deoxy-3-O-(D-2-propionyl-L-alanyl-D-isoglutamine benzyl ester)-α-D-allopyranoside Benzyl 2-acetamido-4,6-O-benzylidene-2-deoxy-3-O-(D-2-propionyl-L-alanyl-D-isoglutamine benzyl ester)-α-D-allopyranoside (305 mg) is stirred in 60% aqueous acetic acid (12 ml) at 90° for 20 minutes. The cooled solution is concentrated and traces of acetic acid are removed by two coevaporations with water followed by two coevaporations with toluene. The residue is triturated with diethyl ether, and the resulting solid is filtered, washed thoroughly with diethyl ether and dried in vacuo to afford benzyl 2-acetamido-2-deoxy-3-O-(D-2-propionyl-L-alanyl-D-isoglutamine benzyl ester)-α-D-alloypyranoside as a white amorphous solid; yield 204 mg (76%). The 300 MHz nmr spectrum in DMSO-d$_6$ is in accord with the desired structure.

Step B: Preparation of benzyl 2-acetamido-2-deoxy-3-O-(D-2-propionyl-L-alanyl-D-isoglutamine benzyl ester)-6-O-stearoyl-α-D-allopyranoside To a solution of benzyl 2-acetamido-2-deoxy-3-O-(D-2-propionyl-L-alanyl-D-isoglutamine benzyl ester)-α-D-allopyranoside (185 mg) in pyridine (9 ml) was added stearoyl chloride (110 μl). After stirring at room temperature for 1 hour, additional stearoyl chloride (20 μl) is added and the solution is stirred at room temperature overnight. Methanol (0.5 ml) is added and stirring is continued for 15 minutes before evaporation to dryness. The residue is dissolved in chloroform (20 ml) and the solution is washed with water (20 ml), dried over anhydrous sodium sulfate, and concentrated to afford a residue which solidifies upon trituration with petroleum ether. The solid is filtered, washed with petroleum ether, and dried in vacuo. The material (162 mg) is taken up in a small volume of chloroform, applied to a column of silica gel (18.5 g), and eluted with 30:1 chloroform-methanol. Fractions containing the desired product are combined and concentrated. The residue is triturated with diethyl ether-petroleum ether to afford benzyl 2-acetamido-2-deoxy-3-O-(D-2-propionyl-L-alanyl-D-isoglutamine benzyl ester)-6-O-stearoyl-α-D-allopyranoside as a white amorphous solid, yield 98 mg (38%), [α]$_D$ +15° (c 0.97, chloroform). The 300 MHz nmr spectrum in DMSO-d$_6$ is was in accord with the desired structure.

Step C: Preparation of 2-acetamido-2-deoxy-3-O-(D-2-propionyl-L-alanyl-D-isoglutamine)-6-O-stearoyl-D-allose A solution of benzyl 2-acetamido-2-deoxy-3-O-(D-2-propionyl-L-alanyl-D-isoglutamine benzyl ester)-6-O-stearoyl-α-D-allopyranoside (79 mg) in glacial acetic acid (10 ml) is hydrogenolyzed overnight in the presence of 10% palladium-on-charcoal (0.3 g). The reaction mixture is filtered through Celite, the filtrate evaporated, and traces of acetic acid removed by several coevaporations with toluene. The residue is taken up in a minimal volume of methanol, applied to a column of silica gel, and eluted successively with 9:1 chloroform-methanol, 80:20:2 chloroform-methanol-water, and 70:40:5 chloroform-methanol-water. Fractions containing the desired product are combined and concentrated, and the residue is taken up in a small volume of water and lyophilized to afford 2-acetamido-2-deoxy-3-O-(D-2-propionyl-L-alanyl-D-isoglutamine)-6-O-stearoyl-D-allose as a white amorphous solid, yield 42 mg (65%). The 300 MHz nmr spectra in D$_2$O and DMSO-d$_6$ are in accord with the desired structure.

EXAMPLE 22

Preparation of 2-acetamido-2-deoxy-3-O-(L-2-propionyl-L-alanyl-D-isoglutamine)-6-O-stearoyl-D-glucose

Step A: Preparation of benzyl 2-acetamido-2-deoxy-3-O-(L-2-propionyl-L-alanyl-D-isoglutamine benzyl ester)-α-D-glucopyranoside Benzyl 2-acetamido-4,6-O-benzylidene-2-deoxy-3-O-(L-2-propionyl-L-alanyl-D-isoglutamine benzyl ester)-α-D-glucopyranoside (124 mg) is stirred in 60% aqueous acetic acid (5 ml) at 90° for 20 minutes. The cooled solution is concentrated and traces of acetic acid are removed by two coevaporations with water followed by two coevaporations with toluene. The residue is triturated with diethyl ether and the resulting solid is filtered, washed thoroughly with diethyl ether, and dried in vacuo to afford benzyl 2-acetamido-2-deoxy-3-O-(L-2-propionyl-L-alanyl-D-isoglutamine benzyl ester)-α-D-glucopyranoside as a white amorphous solid; yield 98 mg (89%). The 300 MHz nmr spectrum in DMSO-d$_6$ is in accord with the desired structure.

Step B: Preparation of benzyl 2-acetamido-2-deoxy-3-O-(L-2-propionyl-L-alanyl-D-isoglutamine benzyl ester)-6-O-stearoyl-α-D-glucopyranoside To a solution of benzyl 2-acetamido-2-deoxy-3-O-(L-2-propionyl-L-alanyl-D-isoglutamine benzyl ester)-α-D-glucopyranoside (94 mg) in pyridine (5 ml) is added stearoyl chloride (56 μl). After stirring at room temperature for 1 hour, additional stearoyl chloride (10 μl) is added and the solution is stirred at room temperature overnight. Methanol (0.5 ml) is added and stirring is continued for 15 minutes before concentrating to dryness. The residue is dissolved in chloroform (20 ml) and the solution is washed with saturated aqueous sodium hydrogen carbonate (20 ml) followed by water (20 ml), dried over anhydrous sodium sulfate, and concentrated to afford a residue which is taken up in a minimal volume of chloroform and applied to a column of silica gel (9.9 g). Elution with 30:1 chloroform-methanol and combination and concentration of the fractions containing the desired product affords benzyl 2-acetamido-2-deoxy-3-O-(L-2-propionyl-L-alanyl-D-isoglutamine benzyl ester)-6-O-stearoyl-α-D-glucopyranoside as an amorphous solid, yield 47 mg (36%). Crystallization is achieved from ethyl acetate-ether-petroleum ether; mp 145°-150°, $[\alpha]_D$ +19° (c, 1.04, CHCl$_3$). The 300 MHz nmr spectrum in DMSO-d$_6$ is in accord with the desired structure.

Step C: Preparation of 2-acetamido-2-deoxy-3-O-(L-2-propionyl-L-alanyl-D-isoglutamine)-6-O-stearoyl-D-glucose A solution of benzyl 2-acetamido-2-deoxy-3-O-(L-2-propionyl-L-alanyl-D-isoglutamine benzyl ester)-6-O-stearoyl-α-D-glucopyranoside (40 mg) in glacial acetic acid (5 ml) is hydrogenolyzed in the presence of 10% palladium-on-charcoal (0.2 g) for 60 hours. The reaction mixture is filtered through Celite, the filtrate evaporated, and traces of acetic acid removed by several coevaporations with toluene. The residue is taken up in a miminal volume of methanol, applied to a column of silica gel (6 g), and eluted with 9:1 chloroform-methanol (20 ml) followed by 80:20:2 chloroform-methanol-water. Fractions containing the desired product are combined and concentrated and the residue is taken up in a small volume of water and lyophilized to afford 2-acetamido-2-deoxy-3-O-(L-2-propionyl-L-alanyl-D-isoglutamine)-6-O-stearoyl-D-glucose as a white amorphous solid; yield 13 mg (40%). The 300 MHz nmr spectra in DMSO-d$_6$ and D$_2$O are in accord with the desired structure.

EXAMPLE 23

Preparation of ethyl 2-acetamido-2-deoxy-3-O-(D-2-propionyl-L-alanyl-D-isoglutamine)-α-D-mannopyranoside

Step A: Preparation of ethyl 2-acetamido-4,6-O-benzylidene-3-O-(D-1-carboxyethyl)-2-deoxy-α-D-mannopyranoside To a stirred solution of ethyl 2-acetamido-4,6-O-benzylidene-2-deoxy-α-D-mannopyranoside (0.95 g) in dry dioxane (80 ml) at 90° is added sodium hydride (0.67 g, 50% oil suspension). After 1 hour the temperature is lowered to 65° and then a solution of L-2-chloropropionic acid (0.46 g) in a small volume of dioxane is added. After one hour additional 50% sodium hydride (2.65 g) is added and stirring at 65° is continued overnight. Water (50 ml) is carefully added to the cooled reaction mixture. The resulting solution is concentrated to a small volume and diluted with water (60 ml). The aqueous mixture is extracted twice with chloroform and filtered through Celite, and then the aqueous layer is acidified to pH~3 at 0° by addition of 2.5 N HCl and extracted with chloroform (3×). The combined chloroform extracts of the acidified aqueous mixture are washed with water, dried over anhydrous magnesium sulfate, and concentrated to afford ethyl 2-acetamido-4,6-O-benzylidene-3-O-(D-1-carboxyethyl)-2-deoxy-α-D-mannopyranoside as a syrup; yield 731 mg (63%). Crystallization is achieved from ethyl acetate-petroleum ether. The 300 MHz nmr spectrum in methanol-d$_4$ is in accord with the desired structure, mp 173°-173.5°, $[\alpha]_D$ +22° (c, 1.06, methanol).

Step B: Preparation of ethyl 2-acetamido-4,6-O-benzylidene-2-deoxy-3-O-(D-2-propionyl-L-alanyl-D-isoglutamine benzyl ester)-α-D-mannopyranoside To a solution of ethyl 2-acetamido-4,6-O-benzylidene-3-O-(D-1-carboxyethyl)-2-deoxy-α-D-mannopyranoside (557 mg) in dry N,N-dimethylformamide (5 ml) at −15° is added N-methylmorpholine (155 μl) and isobutyl chloroformate (180 μl). After stirring 10 minutes at −15°, a pre-cooled solution of L-alanyl-D-isoglutamine benzyl ester hydrochloride (470 mg) in DMF (3 ml) is added followed by N-methylmorpholine (155 μl). The reaction mixture is stirred at −15° for 4 hours and then allowed to warm to 0°. An aqueous solution of potassium hydrogen carbonate (2.5 M, 3 ml) is added dropwise. The mixture is stirred at 0° for 30 minutes and poured into distilled water (80 ml). The aqueous mixture is concentrated to dryness. The residue is taken up in DMF and adsorbed onto silica gel (2.5 g). The mixture is applied to a column of silica gel (50 g) and eluted with 29:1 chloroform-methanol. The fractions containing the desired product are combined and concentrated. Trituration of the residue with diethyl ether affords ethyl 2-acetamido-4,6-O-benzylidene-2-deoxy-3-O-(D-2-propionyl-L-alanyl-D-isoglutamine benzyl ester)-α-D-mannopyranoside as a white crystalline solid; yield 615 mg (65%), mp 162°-164°, $[\alpha]_D$ +13° (c, 1.0, DMF). The 300 MHz nmr spectrum in DMSO-d$_6$ is in accord with the desired structure.

Step C: Preparation of ethyl 2-acetamido-2-deoxy-3-O-(D-2-propionyl-L-alanyl-D-isoglutamine)-α-D-mannopyranoside A solution of ethyl 2-acetamido-4,6-O-benzylidene-2-deoxy-3-O-(D-2-propionyl-L-alanyl-D-isoglutamine benzyl ester)-α-D-mannopyranoside (402 mg) in glacial acetic acid (15 ml) is hydrogenolyzed in the presence of palladium black (0.15 g) at room temperature overnight. The reaction mixture is filtered through Celite, the filtrate evaporated, and traces of acetic acid removed by several coevaporations with water and toluene. The residue is dissolved in a small volume of water and lyophilized to afford ethyl 2-acetamido-2-deoxy-3-O-(D-2-propionyl-L-alanyl-D-isoglutamine)-α-D-mannopyranoside as a white amorphous solid; yield 273 mg (91%), $[\alpha]_D$ +28° (c, 0.50, H$_2$O). The 300 MHz nmr spectrum in D$_2$O is in accord with the desired structure.

EXAMPLE 24

Preparation of 2-acetamido-4,6-di-O-acetyl-2-deoxy-3-O-(D-2-propionyl-L-alanyl-D-isoglutamine)-D-allose

Step A: Preparation of benzyl 2-acetamido-4,6-di-O-acetyl-2-deoxy-3-O-(D-2-propionyl-L-alanyl-D-isoglutamine benzyl ester)-α-D-allopyranoside To a solution of benzyl 2-acetamido-2-deoxy-3-O-(D-2-propionyl-L-alanyl-D-isoglutamine benzyl ester)-α-D-allopyranoside (153 mg) in N,N-dimethylformamide (3 ml) is added pyridine (2 ml) and acetic anhydride (1 ml). The solution is stirred at room temperature for 5 hours, after which additional acetic anhydride (0.5 ml) is added and stirring at room temperature was continued overnight. The solution is then evaporated and coevaporated several times with toluene. After drying the residue under high vacuum, the residue is taken up in a small volume of ethyl acetate, the solution applied to a column of silica gel (20 g), and eluted with 12:1 chloroform-methanol. Combination and evaporation of the appropriate fractions afford benzyl 2-acetamido-4,6-di-O-acetyl-2-deoxy-3-O-(D-2-propionyl-L-alanyl-D-isoglutamine benzyl ester)-α-D-allopyranoside as a white amorphous solid; yield 139 mg (81%). The 300 MHz nmr spectrum in DMSO-$d_6$ is in accord with the desired structure.

Step B: Preparation of 2-acetamido-4,6-di-O-acetyl-2-deoxy-3-O-(D-2-propionyl-L-alanyl-D-isoglutamine)-D-allose A solution of benzyl 2-acetamido-4,6-di-O-acetyl-2-deoxy-3-O-(D-2-propionyl-L-alanyl-D-isoglutamine benzyl ester)-α-D-allopyranoside (125 mg) in glacial acetic acid (6 ml) is hydrogenolyzed at room temperature in the presence of palladium (added in the form of palladium oxide, 0.12 g) for 65 hours. The reaction mixture is filtered through Celite. The filtrate is concentrated and traces of acetic acid are removed by several coevaporations with toluene. The residue is taken up in methanol, a small amount of insoluble material is removed by filtration through sintered glass, and the product is precipitated by addition of diethyl ether. The solid is filtered, dissolved in a small volume of water, and lyophilized to afford 2-acetamido-4,6-di-O-acetyl-2-deoxy-3-O-(D-2-propionyl-L-alanyl-D-isoglutamine)-D-allose as a white amorphous solid; yield 54 mg (57%). The 300 MHz nmr spectrum in $D_2O$ is in accord with the desired structure.

EXAMPLE 25

Preparation of benzyl 2-acetamido-4,6-di-O-acetyl-2-deoxy-3-O-(D-2-propionyl-L-alanyl-D-isoglutamine)-α-D-allopyranoside A mixture of benzyl 2-acetamido-4,6-di-O-acetyl-2-deoxy-3-O-(D-2-propionyl-L-alanyl-D-isoglutamine benzyl ester)-α-D-allopyranoside (50 mg) in ethanol (5 ml) containing acetic acid (0.5 ml) is hydrogenolyzed at room temperature in the presence of 10% palladium-on-charcoal (50 mg) for 24 hours. The reaction mixture is filtered through Celite, the filtrate evaporated, and traces of acetic acid removed by several coevaporations with toluene. The residue is taken up in the minimal volume of methanol, applied to a column of silica gel, and the column developed with 9:1 chloroform-methanol followed by 80:20:2 chloroform-methanol-water. Fractions containing the desired product are combined, evaporated, and the residue is taken up in a small volume of water and lyophilized to afford benzyl 2-acetamido-4,6-di-O-acetyl-2-deoxy-3-O-(D-2-propionyl-L-alanyl-D-isoglutamine)-α-D-allopyranoside; yield 28 mg (64%). The 300 MHz nmr spectrum in DMSO-$d_6$ is in accord with the desired structure.

EXAMPLE 26

Preparation of p-aminophenyl 2-acetamido-2-deoxy-3-O-(L-2-propionyl-L-alanyl-D-isoglutamine)-β-D-glucopyranoside Step A: Preparation of p-nitrophenyl 2-acetamido-4,6-O-benzylidene-3-O-(L-1-carboxyethyl)-2-deoxy-β-D-glycopyranoside To a solution of p-nitrophenyl 2-acetamido-4,6-O-benzylidene-2-deoxy-β-D-glycopyranoside [prepared by the process set forth in R. W. Jeanloz, E. Walker, and P. Sina, *Carbohydr. Res.*, 6, 184 (1968)] (1.2 g) in dry dioxane (250 ml) is added at 95° sodium hydride (400 mg, 50% oil dispersion). After one hour, the temperature is lowered to 65° and then a solution of D-2-chloropropionic acid (1.1 g) in a small volume of dry dioxane is added. After one hour, additional 50% sodium hydride (1 g) is added, and stirring at 65° is continued overnight. Water (70 ml) is added to the cooled mixture to decompose excess sodium hydride. A dark-colored lower layer which develops is discarded, and the upper layer is filtered, partially concentrated, and diluted with water (150 ml). The aqueous mixture is extracted with chloroforom, and the aqueous layer is filtered and acidified to pH 3 at 0° by addition of 2.5 N HCl. The resulting precipitate is extracted with chloroform, the combined organic extracts dried (magnesium sulfate), and evaporated to a residue that is dissolved in warm methanol (40 ml) and the product precipitated by addition of water. The solid is filtered and dried in vacuo over phosphorus pentoxide to afford p-nitrophenyl 2-acetamido-4,6-O-benzylidene-3-O-(L-1-carboxyethyl)-2-deoxy-β-D-glucopyranoside as a white powder; yield 383 mg. The 300 MHz nmr spectrum in chloroform-d is in accord with the desired structure.

Step B: Preparation of p-nitrophenyl 2-acetamido-4,6-O-benzylidene-2-deoxy-3-O-(L-2-propionyl-L-alanyl-D-isoglutamine benzyl ester)-β-D-glucopyranoside To a solution of p-nitrophenyl 2-acetamido-4,6-O-benzylidene-3-O-(L-1-carboxyethyl)-2-deoxy-β-D-glucopyranoside (357 mg) in dry N,N-dimethylformamide (4 ml) at −15° are added successively N-methylmorpholine (79 μl) and isobutyl chloroformate (93 μl). After stirring 3 minutes at −15° a pre-cooled solution of L-alanyl-D-isoglutamine benzyl ester hydrochloride (285 mg) in dry DMF (2 ml) is added. The reaction mixture is stirred at −15° for 2 hours and the temperature increased to 0°. An aqueous solution of potassium hydrogen carbonate (2.5 M, 3 ml) is added dropwise and the mixture is stirred at 0° for 30 minutes and then poured into distilled water (100 ml). The precipitated solid is filtered, the solid washed thoroughly with water and then diethyl ether. After drying in vacuo over phosphous pentoxide, p-nitrophenyl 2-acetamido-4,6-O-benzylidene-2-deoxy-3-O-(L-2-propionyl-L-alanyl-D-isoglutamine benzyl ester)-β-D-glycopyranoside is obtained as a white solid; yield 523 mg (93%). The 300 MHz nmr spectrum in DMSO-$d_6$ is in accord with the desired structure.

Step C: Preparation of p-nitrophenyl 2-acetamido-2-deoxy-3-O-(L-2-propionyl-L-alanyl-D-isoglutamine benzyl ester)-β-D-glucopyranoside A mixture of p-nitrophenyl 2-acetamido-4,6-O-benzylidene-2-deoxy-3-O-(L-2-propionyl-L-alanyl-D-isoglutamine benzyl ester)-β-D-glucopyranoside (514 mg) in 60% aqueous acetic acid (40 ml) is stirred at 90° for 30 minutes. The resulting solution is then evaporated and coevaporated several times with toluene to remove traces of acetic acid. After drying in vacuo over phosphrous pentoxide, p-nitrophenyl 2-acetamido-2-deoxy-3-O-(L-2-propionyl-L-alanyl-D-isoglutamine benzyl ester)-β-D-glucopyranoside is obtained as a white solid; yield 328 mg (72%). The 300 MHz nmr spectrum in methanol-$d_4$ is in accord with the desired structure.

Step D: Preparation of p-aminophenyl 2-acetamido-2-deoxy-3-O-(L-2-propionyl-L-alanyl-D-isoglutamine)-β-D-glucopyranoside A solution of p-nitrophenyl 2-acetamido-2-deoxy-3-O-(L-2-propionyl-L-alanyl-D-isoglutamine benzyl ester)-β-D-glucopyranoside (310 mg) in glacial acetic acid (10 ml) is hydrogenolyzed in the presence of 5% palladium-on-charcoal (300 mg) at room temperature overnight. The catalyst is removed by filtration through Celite, the filtrate is evaporated and co-evaporated several times with toluene. The residue is dissolved in the minimal volume of methanol, and the solution is applied to a column of silica gel (30 g). Development is effected with at first 9:1 chloroform-methanol, then 80:20:2 chloroform-methanol-water, and finally with 60:40:10 chloroform-methanol-water. The fractions containing pure product are combined and evaporated to a residue that is taken up in a little methanol and the product precipitated by addition of diethyl ether. The solid is filtered and dried in vacuo over phosphorus pentoxide to afford p-aminophenyl 2-acetamido-2-deoxy-3-O-(L-2-propionyl-L-alanyl-D-isoglutamine)-β-D-glucopyranoside as a white solid; yield 169 mg (66%). The 300 MHz nmr spectrum in $D_2O$ is in accord with the desired structure.

EXAMPLE 27

This example shows the use of the adjuvants of the present invention in formulating influenza vaccines. An aqueous suspension of the final product of the example indicated in Column I in phosphate buffered saline is added in the level indicated in column II to a sample of bivalent whole influenza vaccine having the total amount of antigen indicated in column III. The total volume of the completed vaccine is shown in column IV.

| I | II (mg) | III (mg) | IV |
|---|---|---|---|
| 1 | 0.001 | 0.5 | 0.25 |
| 2 | 0.005 | 0.3 | 0.25 |
| 3 | 0.01 | 0.1 | 0.25 |
| 4 | 0.05 | 0.05 | 0.25 |
| 5 | 0.1 | 0.01 | 0.25 |
| 6 | 0.001 | 0.01 | 0.5 |
| 7 | 0.005 | 0.05 | 0.5 |
| 8 | 0.01 | 0.1 | 0.5 |
| 9 | 0.05 | 0.3 | 0.5 |
| 10 | 0.1 | 0.5 | 0.75 |
| 11 | 0.001 | 0.5 | 0.75 |
| 12 | 0.005 | 0.3 | 0.75 |
| 13 | 0.01 | 0.1 | 0.75 |
| 14 | 0.05 | 0.05 | 0.75 |
| 15 | 0.1 | 0.01 | 0.75 |
| 16 | 0.001 | 0.01 | 0.75 |
| 17 | 0.005 | 0.05 | 0.75 |
| 18 | 0.01 | 0.1 | 0.75 |
| 19 | 0.05 | 0.3 | 0.75 |
| 20 | 0.1 | 0.5 | 0.75 |
| 21 | 0.001 | 0.5 | 0.75 |
| 22 | 0.005 | 0.3 | 1.0 |
| 23 | 0.01 | 0.1 | 1.0 |
| 24 | 0.05 | 0.05 | 1.0 |
| 25 | 0.1 | 0.01 | 1.0 |
| 26 | 0.2 | 0.01 | 1.0 |

EXAMPLE 28

A group of 10 mice are injected with 0.1 ml of a saline solution containing 100 μg of the compound of Example 1. Seven days later the mice are challenged with a lethal dose of meningococcal B protein and meningococcal polysaccharides types A and B in 5% hog gastric mucin. In replicate tests the survival rate 72 hours post challenge is from 40–50%.

What is claimed is:

1. A composition comprising a vaccine for human or animal administration and an antibacterially effective amount of a 2-amino-2-deoxy-glycose compound of the general structural formula:

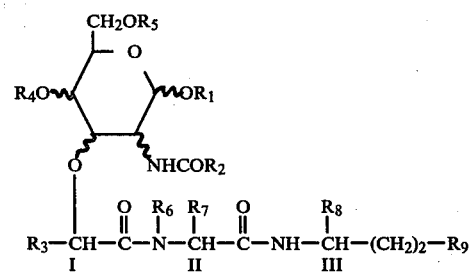

provided said glycose is not 2-amino-2-deoxy-D-glucose, wherein $R_1$ is hydrogen, alkyl of 1 to 7 carbon atoms optionally substituted by hydroxy, mercapto, alkoxy of 1 to 3 carbon atoms, alkyl mercapto of 1 to 3 carbon atoms, hydroxy or mercapto esterified by an acid of 1 to 4 carbon atoms, halogen, carboxyl, carboxyl esterified by an alcohol of 1 to 3 carbon atoms, or amidated carboxyl, phenyl, benzyl, each optionally substituted by alkyl of 1 to 3 carbon atoms, lower alkyldioxy, amino, trifluoromethyl, hydroxy, mercapto, hydroxy or mercapto etherified by alkyl of 1 to 3 carbon atoms, or hydroxy or mercapto esterified by an acid of 1 to 4 carbon atoms;

$R_2$ is alkyl of 1 to 7 carbon atoms optionally substituted by hydroxy, mercapto, alkoxy of 1 to 3 carbon atoms, alkyl mercapto of 1 to 3 carbon atoms, hydroxy or mercapto esterified by an acid of 1 to 4 carbon atoms, halogen, carboxyl, carboxyl esterified by an alcohol of 1 to 3 carbon atoms, or amidated carboxyl, phenyl, optionally substituted by alkyl of 1 to 3 carbon atoms, lower alkyldioxy, amino, trifluoromethyl, hydroxy, mercapto, hydroxy or mercapto etherified by alkyl of 1 to 3 carbon atoms, or hydroxy or mercapto esterified by an acid of 1 to 4 carbon atoms;

$R_3$ is H or alkyl of 1 to 10 carbon atoms;

$R_4$ and $R_5$ are same or different and are
hydrogen, alkanoyl of 2 to 21 carbon atoms,
benzoyl, naphthoyl-1 or naphthoyl-2 each optionally substituted by halogen, alkyl of 1 to 3 carbon atoms, alkoxy of 1 to 3 carbon atoms, trifluoromethyl, hydroxy or alkanoyloxy of 1 to 3 carbons,
an alkanesulfonic acid of 1 to 7 carbon atoms, or a phenylsulfonic acid optionally substituted by alkyl of 1 to 3 carbon atoms,
carbamoyl, alkyl carbamoyl of 1 to 3 carbon atoms, phenylcarbamoyl or napththylcarbamoyl;

$R_6$ is H or $R_6$-$R_7$ together is —$CH_2$—$CH_2$—$CH_2$—;

$R_7$ is H, alkyl of 1 to 7 carbon atoms, hydroxymethyl, mercaptomethyl, benzyl; or substituted benzyl wherein the substituents are the same as defined for $R_1$;

$R_8$ and $R_9$ each is carboxyl, esterified carboxyl of 1 to 7 carbon atoms, amidated carboxyl, or mono- or dialkyl amidated carboxyl wherein the alkyl group has 1 to 3 carbon atoms;

provided that when $R_3$ is lower alkyl, the stereochemistry at asymmetric center I can be either D or L, when $R_7$ is not H, the stereochemistry at asymmetric center II is either L or D, and the stereochemistry at asymmetric center III is D.

2. A composition comprising a vaccine for human or animal administration and an amount of a 2-amino-2-deoxy-glycose compound according to claim 1 wherein the compound is present in an amount effective to exert an adjuvant effect.

* * * * *